United States Patent [19]

Marsili

[11] Patent Number: 4,962,195
[45] Date of Patent: Oct. 9, 1990

[54] SOLVATE OF CEFADROXYL

[75] Inventor: Leonardo Marsili, Milan, Italy

[73] Assignee: Rifar S.R.L., Milan, Italy

[21] Appl. No.: 323,129

[22] Filed: Mar. 13, 1989

Related U.S. Application Data

[63] Continuation of Ser. No. 43,494, Apr. 28, 1987, abandoned.

[51] Int. Cl.$^5$ ............................................. C07D 501/22
[52] U.S. Cl. ...................................................... 540/230
[58] Field of Search ................................. 540/230, 228

[56] References Cited

U.S. PATENT DOCUMENTS 4,504,657  3/1985  Marsili .................................. 540/230

OTHER PUBLICATIONS

Chemical Abstracts vol. 96 74631k (1982).

*Primary Examiner*—Nicholas S. Rizzo
*Attorney, Agent, or Firm*—Oblon, Spivak, McClelland, Maier & Neustadt

[57] ABSTRACT

The invention relates to a novel crystalline cefadroxyl hemihydrate having a K.F. between about 3.5 and 2.0%: such compound is more stable than other cefadroxyl molecules.

The novel cefadroxyl is obtained preparing and isolating a novel cefadroxil solvate of dimethylacetamide, or of N-methyl-2-pyrrolidone or of monomethylformamide, slurrying said solvate with a mixture methanol/isopropyl alcohol 30:70 to 50:50 by volume at a temperature of about +45° C. to +55° C. and then filtering the so obtained compound.

2 Claims, No Drawings

SOLVATE OF CEFADROXYL

This application is a continuation of application Ser. No. 043,494, filed on Apr. 28, 1987, now abandoned.

DESCRIPTION

The present invention relates to a novel crystalline cefadroxil and to a method for producing it.

Cefadroxil is a well known antibiotic substance having antibacterial activity: it is disclosed and claimed in the U.S. Pat. No. 3,489,752 according to which it is obtained by acylation of 7-ADCA with an amino-protected derivative of D(−)-alpha-p-hydroxyphenylglycine. U.S. Pat. No. 3,985,741 discloses preparation of cefadroxil by acylation of 7-ADCA with mixed anhydride of D-(−)-alpha-p-hydroxyphenylglycine when the latter's alpha-amino group has been blocked with a beta-keto compound such as methyl acetoacetate: the reaction mixture is first added with water and then with dimethylformamide to precipitate a crystallized solvate of cefadroxil having more than 3% of water content which, after filtration, is slurried in 90% methanol.

U.S. Pat. No. 4,504,657 describes and claims a different form of cefadroxil, which is the crystalline cefadroxil monohydrate having a well defined X-ray diffraction pattern characterizing said compound: this crystalline cefadroxil monohydrate is obtained (see also the U.S. Pat. No. RE 31,730) by acylation of silylated 7-ADCA with D(−)-alpha-p-hydroxyphenylglycine chloride hydrochloride. The reaction mixture is added first with water and then with dimethylformamide to precipitate the dimethylformamide solvate which after filtration is treated with water or a water/solvent mixture to cleave the solvate and to precipitate the desired final compound.

The present invention relates to a novel crystalline cefadroxil having a water content of about 3% and characterized by the following X-ray diffraction properties:

| Spacing d(Å) | Relative Intensity |
| --- | --- |
| 10.59 | 30 |
| 8.68 | 100 |
| 8.03 | 43 |
| 7.14 | 39 |
| 6.72 | 41 |
| 6.18 | 40 |
| 5.67 | 11 |
| 5.49 | 23 |
| 4.83 | 69 |
| 4.71 | 52 |
| 4.65 | 25 |
| 4.23 | 57 |
| 4.13 | 55 |
| 3.98 | 74 |
| 3.87 | 33 |
| 3.80 | 36 |
| 3.31 | 30 |
| 3.02 | 15 |
| 2.95 | 18 |
| 2.88 | 25 |
| 2.64 | 25 |
| 2.55 | 19 |
| 2.52 | 17 |
| 2.48 | 14 |
| 2.43 | 15 |
| 2.31 | 16 |
| 2.14 | 13 |
| 2.04 | 9 |

This novel cefadroxil which in the following will be called "cefadroxil hemihydrate" has shown to be more stable than the knwon crystalline cefadroxil monohydrate.

The cefadroxil hemihydrate is obtained by adding to an aqueous solution containing cefadroxil just prepared from 7-ADCA a solvent selected from the group consisting of dimethylacetamide, N-methyl-2-pyrrolidone, monomethylformamide, while controlling the pH of the solution in the range 5.5–6, to give the corresponding cefadroxil solvate which precipitates and is filtered off and which after drying is slurried with a mixture methanol-isopropyl alcohol 30:70 to 50:50 by volume at a temperature in the range of about +45° C. to +55° C., the desired cefadroxil hemihydrate being isolated by filtration.

All known methods for transforming the 7-ADCA into the mentioned aqueous solution containing cefadroxil can be used: for instance, it is possible to follow the procedures described in Example XVI of the European patent application No. 001,133, or in Examples 1 and 2 of the U.K. patent application No. 2,064,511 or in Examples 1 to 4 of the U.S. Pat. No. 4,234,721.

Attempts have been made to use also the known cefadroxil-dimethylformamide solvate (see the U.S. Pat. Nos. 3,985,741, 4,504,657 and Re 31,730) but it was impossible to obtain the desired final cefadroxil hemihydrate (always the known crystalline cefadroxil monohydrate was isolated): this appears to be due to the fact that the cefadroxil-DMF solvate has a K.F. value of 1.8% or more, as it is written also in Example 6A of U.S. Pat. No. 3,985,741 and in Example 2A of the U.S. Pat. No. 4,234,721.

The use of the cefadroxil solvates of dimethylacetamide, of N-methyl-2-pyrrolidone and of monomethylformamide is therefore critical, what may be due to their very low water content (<1.0%); such solvates are novel and essential intermediates for the production of the cefadroxil hemihydrate and therefore they are part of the present invention and are here claimed per se.

Also the use of the mixture methanol/isopropyl alcohol has proved to be essential: indeed, if ethyl alcohol is used, the cefadroxil molecule is decomposed; if methanol alone is used, the molecule of the final cefadroxil retains an exceedingly high amount of the same methanol (more than 0.4%), what is unacceptable in consequence of its toxicity. This has proved to be true also in the case that methanol is used in mixture with other alcohols wherein the methanol content is too high.

The isopropyl alcohol does not decompose the cefadroxil molecule and its toxicity is much lower than that of methanol, but it has been found that it cannot be used alone because it is impossible to obtain pure crystalline cefadroxil hemihydrate.

It has been surprisingly found that if isopropyl alcohol is additioned with methanol in an amount of 50 to 70% of isopropyl alcohol and 50 to 30% of methanol, the novel crystalline cefadroxil hemihydrate with a methanol content lower than 0.010% (corresponding to 100 ppm) is obtained.

The invention is illustrated by the following examples in which the NMR spectra were recorded in D$_2$O solution (15 mg/ml) on a Varian XL-300 spectrometer.

EXAMPLE 1

Cefadroxil Dimethylacetamide Solvate

7-ADCA (45 g) was added to methylene chloride (700 ml) at room temperature. Triethylamine (35.5 g)

was added over 15' with stirring at a temperature below 25° C. Trimethylchlorosilane (43.2 g) was then dropped over a 30' period. The mixture was stirred at 30° C. for 90' and then cooled to −10° C.

Dimethylaniline (31 g) and D(−)-p-hydroxyphenylglycyl chloride hydrochloride hemidioxane solvate (63 g) were added and the mixture was stirred at −5° C./0° C. for about 90'. Water (170 ml) was added and the reaction mixture was stirred for 30'. The aqueous phase was diluted with dimethylacetamide (350 ml) and the pH was adjusted to 6.0 by slowly adding diethylamine at 25° C. The mixture was stirred at 20° C. for 120'. The cefadroxil dimethylacetamide solvate was collected by filtration, washed with dimethylacetamide/water 2:1 then with acetone to yield, after drying at 40° C., 81.3 g of the title compound.

K.F.: 0.51%.

HPLC Assay: 69.3% on dry basis.

PMR: 6.9–7.35 δ (m,C$_6$H$_4$—); 5.59 δ [d, C(7)-H]; 5.15 δ (s,C$\underline{H}$—CO); 4.98 δ [d, C$\underline{H}$-S]; 3.02–3.42 δ (m, S—C$\underline{H}_2$); 1.8 δ (s, CH$_3$) characteristic of cefadroxil moiety and the following peaks due to the solvent: 2.83–3.01 δ (s,s, N(CH$_3$)$_2$); 2.04 δ (d,COCH$_3$).

$^{13}$C-NMR: 21.07 δ [$\underline{C}$H$_3$—C=]; 30.93 δ [$\underline{C}$H$_2$-S]; 58.78 δ [$\underline{C}$H—NH$_2$]; 59.51 δ [$\underline{C}$H-S]; 61.16 δ [NH—$\underline{C}$H—CO];

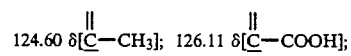

124.60 δ[$\underline{C}$—CH$_3$]; 126.11 δ[$\underline{C}$—COOH];

166.21 δ [CO, β-lactam]; 172.37 δ [$\underline{C}$OOH]; 172.58 δ [$\underline{C}$O—NH]; 129.05 δ, 132.7 δ, 118.99 δ, 160.45 δ [aromatic carbon atoms] characteristic of Cefadroxil moiety and the following peaks due to the solvent: 23.15 δ [CO—$\underline{C}$H$_3$]; 37.93 δ [N—$\underline{C}$H$_3$]; 40.85 δ [N—$\underline{C}$H$_3$]; 176.74 δ [$\underline{C}$O].

EXAMPLE 2

Cristalline Cefadroxil hemihydrate

Cefadroxil dimethylacetamide solvate (50 g) prepared according to Example 1 was slurried in a mixture of isopropyl alcohol (250 ml) and methanol (120 ml) at 48°–50° C.

After 120' the mixture was cooled to 10° C., filtered and washed with acetone to yield 34.5 g of crystalline Cefadroxil hemihydrate. K.F.: 2.8%.

Methanol: 0.009%.

Isopropyl alcohol: 0.17%.

HPLC assay: 99.1% on dry basis.

The powder exhibits the following X-ray diffraction properties determined with the radiation (wave lenght: Lambda 1.54051 Angstrom) produced with a Cu/Ni X-ray tube:

| Spacing d(Å) | Relative Intensity |
| --- | --- |
| 10.59 | 30 |
| 8.68 | 100 |
| 8.03 | 43 |
| 7.14 | 39 |
| 6.72 | 41 |
| 6.18 | 40 |
| 5.67 | 11 |
| 5.49 | 23 |
| 4.83 | 69 |
| 4.71 | 52 |
| 4.65 | 25 |
| 4.23 | 57 |
| 4.13 | 55 |
| 3.98 | 74 |
| 3.87 | 33 |
| 3.80 | 36 |
| 3.31 | 30 |
| 3.02 | 15 |
| 2.95 | 18 |
| 2.88 | 25 |
| 2.64 | 25 |
| 2.55 | 19 |
| 2.52 | 17 |
| 2.48 | 14 |
| 2.43 | 15 |
| 2.31 | 16 |
| 2.14 | 13 |
| 2.04 | 9 |

EXAMPLE 3

Cefadroxil Monomethylformamide Solvate

7-ADCA (30 g) was added to methylene chloride (450 ml), trimethylchlorosilane (28.8 g) was added and the mixture was stirred for 10'. Triethylamine (23.7 g) was then dropped over a 30' period while temperature was allowed to reach 30° C. The mixture was stirred 2 hours at 30° C. and then cooled to −10° C.

Bis-trimethyl-silyl-urea (21 g) and D(−)-p-hydroxyphenylglycyl chloride hydrochloride hemidioxane solvate (45 g) were added and the mixture was allowed to react at −5° C. for 90'. After additional 30' stirring at 0° C., water (115 ml) was added.

The reaction mixture was stirred for 30', the aqueous layer cooled to 5° C. and diluted with monomethylformamide (240 ml). Triethylamine was added slowly over 60' and the pH was adjusted to 5.7 at 20° C. After stirring for 2 hours the slurry was filtered, the filter cake washed with monomethylformamide/water 2:1 and then with acetone to yield, after drying at 40° C., 49 g of the title compound:

K.F.: 0.9%.

HPLC Assay: 79.8% on dry basis.

PMR: besides the peaks characteristic of Cefadroxil moiety shown in example 1, the following peaks are due to the solvent 7.98 δ [s, HCO]; 2.71 δ cis [s, NHCH$_3$].

$^{13}$C-NMR: besides the peaks characteristic of Cefadroxil moiety shown in Example 1, the following peaks are due to the solvent: 27.07 δ [$\underline{C}$H$_3$]; 167.6 δ [H—$\underline{C}$O].

EXAMPLE 4

Crystalline Cefadroxil hemihydrate

Cefadroxil monomethylformamide solvate (30 g) prepared according to Example 3 was slurried in 150 ml of a mixture 1:1 of methanol and isopropyl alcohol at 52° C. After 70' at 52° C. the mixture was cooled to 10° C., filtered and washed with acetone to yield 23.2 g of crystalline cefadroxil hemihydrate.

K.F.: 2.9%.

HPLC Assay: 99.6% on dry basis.

Methanol: 0.008%.

Isopropyl alcohol: 0.15%.

The powder exhibits the same X-ray diffraction properties of the product obtained in Example 2.

EXAMPLE 5

Cefadroxil Dimethylacetamide Solvate

Potassium methyl Dane salt of D(−)-p-hydroxyphenylglycine (30.3 g) was added to acetone (170 ml) and the mixture was cooled to −40° C.

Ethylchlorocarbonate (11.15 g) and N-methylmorpholine (0.25 ml) were added at −40° C. The temperature was kept at −35° C. for 120′ and then the mixture was cooled to −55° C.

7-ADCA (21.5 g) was charged at +5° C. into water (50 ml) and dimethylsuphoxide (90 ml) and triethylamine (11.3 g) were added. The obtained solution was cooled to 0° C. and the suspension of mixed anhydride (at −55° C.) was added to the solution of 7-ADCA.

The mixture was stirred at −25° C. for 60′; the temperature was raised to 0° C. and HCl 37% was added slowly during 60′ to a constant pH 1.8. Methylene chloride (175 ml), was added and the mixture was stirred for 15′. The upper layer was diluted with dimethylacetamide (170 ml) and acetone (70 ml), the pH was adjusted to 6.5 at 0° C. with triethylamine. The mixture was stirred at 0° C. for 2 hours. The solvate was washed with dimethylacetamide/water 2:1 and then with acetone to yield 40.5 g of the title compound after drying at 40° C.

K.F.: 0.63%.

HPLC Assay: 69.1% on dry basis.

EXAMPLE 6

Cefadroxil 1-Methyl-2-pyrrolidone Solvate

7-ADCA (30 g) was reacted according to the procedure described in Example 1 using 1-methyl-2-pyrrolidone instead of dimethylacemide. Yield: 52 g.

K.F.: 0.85%.

HPLC Assay: 68.7% on dry basis.

PMR: besides the peaks characteristic of Cefadroxil moiety shown in Example 1, the following peaks are due to the solvent 3.45 $\delta$ [t, $CH_2(5)$]; 2.36 $\delta$ [t, $CH_2(3)$]; 1.98 $\delta$ [q, $CH_2(4)$]; 2.84 $\delta$ [s, N—$CH_3$)].

$^{13}$C-NMR: besides the peaks characteristic of Cefadroxil moiety shown in example 1, the following peaks are due to the solvent: 19.71 $\delta$ [$CH_2(4)$]; 32.27 $\delta$ [N, $CH_3$]; 33.45 $\delta$ [$CH_2(3)$]; 52.97 $\delta$ [$CH_2(5)$]; 180.84 $\delta$ [$CO(2)$].

EXAMPLE 7

Crystalline Cefadroxil hemihydrate

Cefadroxil 1-methyl-2-pyrrolidone solvate (30 g) was slurried in a mixture of 110 ml isopropyl alcohol and 40 ml of methanol kept at 45°–48° C. for 100′. After cooling to 10° C. the mixture was filtered, the product washed with acetone and dried at 40° C.

Yield: 19.5 g of hemihydrate product.

K.F.: 2.5%.

HPLC Assay: 98.2% on dry basis.

Methanol: 0.009%.

Isopropyl alcohol: 0.18%.

I claim:

1. Cefadroxyl solvate of N-methyl-2-pyrrolidone.
2. The cefadroxyl solvate of claim 1, which has a water content of less than 1.0%.

* * * * *